(12) United States Patent
Swann

(10) Patent No.: US 9,636,251 B2
(45) Date of Patent: May 2, 2017

(54) METHOD AND APPARATUS FOR ENDOMETRIAL ABLATION IN COMBINATION WITH INTRAFALLOPIAN CONTRACEPTIVE DEVICES

(75) Inventor: Betsy Swann, Grass Valley, CA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1231 days.

(21) Appl. No.: 12/577,112

(22) Filed: Oct. 9, 2009

(65) Prior Publication Data
US 2011/0083673 A1    Apr. 14, 2011

(51) Int. Cl.
A61F 6/06 (2006.01)
A61F 6/22 (2006.01)
A61B 18/14 (2006.01)
A61B 17/42 (2006.01)
A61B 18/00 (2006.01)

(52) U.S. Cl.
CPC .......... *A61F 6/225* (2013.01); *A61B 18/1492* (2013.01); *A61B 2017/4216* (2013.01); *A61B 2018/00214* (2013.01); *A61B 2018/00559* (2013.01); *A61B 2018/00577* (2013.01)

(58) Field of Classification Search
CPC ...... A61F 6/22; A61F 6/06; A61F 6/00; A61F 6/14; A61B 2017/4233; A61B 2017/1209; A61B 17/42; A61B 2018/00577; A61B 2018/00875; A61M 25/04
USPC ..................... 128/831; 606/28, 34
See application file for complete search history.

(56) References Cited

U.S. PATENT DOCUMENTS

| | | | |
|---|---|---|---|
| 6,526,979 B1 | 3/2003 | Nikolchev et al. | |
| 6,705,323 B1 | 3/2004 | Nikolchev et al. | |
| 6,709,667 B1 | 3/2004 | Lowe et al. | |
| 6,763,833 B1 | 7/2004 | Khera et al. | |
| 6,813,520 B2 | 11/2004 | Truckai et al. | |
| 2003/0093070 A1 | 5/2003 | Strul et al. | |
| 2004/0127932 A1 | 7/2004 | Shah | |
| 2005/0182397 A1 | 8/2005 | Ryan | |
| 2005/0274384 A1* | 12/2005 | Tran et al. | 128/831 |
| 2007/0208213 A1 | 9/2007 | Swann | |
| 2008/0154256 A1* | 6/2008 | Payne et al. | 606/34 |
| 2009/0056722 A1 | 3/2009 | Swann | |

OTHER PUBLICATIONS

U.S. Appl. No. 60/765,262, filed Feb. 3, 2006, Swann, Susan E.
Abbott, J.A., et al., "Quality of life should be considered the primary outcome for measuring success of endometrial ablation" J Am Assoc Gynecol Laparosc, Nov. 2003, pp. 491-495, discussion 495, vol. 10, No. 4. (Abstract).

(Continued)

*Primary Examiner* — Ophelia A Hawthorne
*Assistant Examiner* — Caitlin Carreiro

(57) ABSTRACT

Systems and methods for treating a female reproductive system are disclosed. An intrafallopian device, which may be at least partially non-conductive, is delivered to a fallopian tube. A subsequent uterine ablation may be performed. The ablation element may include insulators at portions of the ablation element contactable with a fallopian tube or intrafallopian device.

13 Claims, 11 Drawing Sheets

(56) References Cited

OTHER PUBLICATIONS

Bongers, M.Y., et al., "Bipolar radio frequency endometrial ablation compared with balloon endometrial ablation in dysfunctional uterine bleeding: impact on patients' health-related quality of life" Fertil Steril, Mar. 2005, pp. 724-734, vol. 83, No. 3. (Abstract).
Brennan, Mairin, "Suite of Shape-Memory Polymers" News of the Week, Materials, Feb. 5, 2001, vol. 79, No. 6.
Chen, Chun-Cheng R., et al., "Optimizing Needle Palcement in Treatment Planning of Radiofrequency Ablation" 2006, 7 pages, Vanderbilt University, Department of Biomedical Engineering, Nashville, TN.
"Conceptus: What is Essure? Frequently Asked Questions" accessed at http://www.essuremd.com/hcp.faq.aspx on Apr. 11, 2006, 10 pages.
"Conceptus: What is Essure? Is it right for me?" accessed at http://www.conceptus.com/Home/Deciding/IsitRightforMe/tabid/61/Default.aspx on Apr. 11, 2006, 1 page.
"Conceptus: What is Essure?" accessed at http://www.conceptus.com/what_is_essure.html on Apr. 11, 2006, 2 pages.
"Endometrial Ablation" 2005, 4 pages, Georgia Reproductive Specialists, accessed at http://www.ivf.com/eablate.html.
"Endometrial Ablation: Procedure Overview" webpage update Feb. 13, 2006, 7 pages, Medical University of South Carolina website, Diagnostic & Surgical Tests & Procedures, http://www.muschealth.com/gs/TandP.aspx?PageIDS=P07774, accessed Apr. 11, 2006.
Finn, Robert, "Essure safe in combo with endometrial ablation" Dec. 15, 2004, 3 pages, OB/GYN News, accessed at http://www.looksmartmom.com/p/articles/mi_m0CYD/is_24_39/ai_n8697311.
Gall, Ken, et al. "Internal stress storage in shape memory polymer nanocomposites" America Institute of Physics, Applied Physics Letters, Jul. 12, 2004, 3 pages, vol. 85, No. 2.
Garry, R., et al., "A comparison of goserelin and danazol as endometrial thinning agents prior to endometrial laser ablation" Br J Obstet Gynaecol, Apr. 1996, p. 103. (Abstract).
Hidlebaugh, D.A., "Relative costs of gynecologic endoscopy vs traditional surgery treatment of abnormal uterine bleeding" AM J Manag Care, Sp. 25, 2001 vol. 7, Spec No. SP31-7.
Indman, M.D., Paul D., "Endometrial Ablation" 3 pages, accessed at http://www.gynalternatives.com/ablation.htm on Apr. 11, 2006.
Lee, J.M., et al., "Wet radio-frequency ablation using multiple electrodes: comparative study of bipolar versus monopolar modes in the bovine liver" Eur J Radiol, Jun. 2005, pp. 408-417, vol. 54, No. 3. (Abstract).
Lethaby, A., et al., "Endometrial destruction techniques for heavy menstrual bleeding" Cochrane Database Syst Rev, Oct. 19, 2005, No. 4, CD001501, update of Cochrane Database Syst Rev, 2002, No. 2, CD001501. (Abstract).
Lim, Issel Anne L., "Biocompatibility of Stent Materials" MIT Undergraduate Research Journal, 2004, pp. 33-37, , vol. 11.
Moseley, H., et al., "Stray RF field strength during radiofrequency endometrial ablation" J Med Eng Technol. May-Jun. 1996, pp. 127-133, vol. 20, No. 3. (Abstract).
Moyer, Paula, "ACOG: Combining In-Office Sterilization and Endometrial Ablation" May 11, 2005, 2 pages, MedPage Today, accessed at http://www.medpagetoday.com/tbprint.cfm?tbid=1022.

Onbargi, L.C., et al., "Efffects of power and electrical current density variations in an in vitro endometrial ablation" Obstet Gynecol. Dec 1993, pp. 912-918, vol. 82, No. 6.
Pasic, Resad P, et al., "A Practical manual of Hysteroscopy and Endometrial Ablation Techniques: A Clinical Cookbook" 2004, pp. 1-33, Taylor & Francis Group.
Pasic, Resad P, et al., "A Practical manual of Hysteroscopy and Endometrial Ablation Techniques: A Clinical Cookbook" 2004, pp. 155-218, Taylor & Francis Group.
Pasic, Resad P, et al., "A Practical manual of Hysteroscopy and Endometrial Ablation Techniques: A Clinical Cookbook" 2004, pp. 219-228, Taylor & Francis Group.
Pasic, Resad P, et al., "A Practical manual of Hysteroscopy and Endometrial Ablation Techniques: A Clinical Cookbook" 2004, pp. 34-139, Taylor & Francis Group.
Pasic, Resad P., et al., "A Practical manual of Hysteroscopy and Endometrial Ablation Techniques: A Clinical Cookbook" 2004, pp. 34-139 and 210-228.
PCT International Search Report and Written Opinion for International Application No. PCT/US2010/049186, mailed Feb. 11, 2011, 17 pages.
PCT Invitation to Pay Additional Fees for International Application No. PCT/US2010/049186, mailed Nov. 3, 2010, 7 pages.
Pellicano, M., et al., "Hysteroscopic transcervical endometrial resection versus thermal destruction for menorrhagia: a prospective randomized trial on satisfaction rate" AM J Obstet Gynecol, Sep. 2002, pp. 545-550, vol. 187, No. 3. (Abstract).
Prior M.V., et al., "Treatment of menorrhagia by radiofrequency heating" Int J Hyperthermia, Mar.-Apr. 1991, pp. 213-220, vol. 7, No. 2. (Abstract).
"Radio Frequency Ablation" 2 pages, Univeristy of Southern California Department of Surgery, accessed at http://www.surgery.usc.edu/divisions/hep/radiofrequencyablation.html.
Seymour, J., et al., "The cost of microwave endometrial ablation under different anaesthetic and clinical settings" BJOG, Oct. 2003, pp. 922-926, vol. 110, No. 10.
"Shape Memory Polymer (SMP) for Medical and Industrial Applications" 1 page, Lawrence Livermore National Laboratory, UCRL-MI-124572.
Valle, R.F., "Concomitant Tubal Sterilization and Endometrial Ablation Safe" May 11, 2005, 2 pages, Contemporary OB/GYN Newsline Meeting News, accessed at http://mediwire.skyscape.com/main/Default.aspx?P=Content&ArticleIDS=160828 on Apr. 11, 2006.
Van Zon-Rabelink, I.A., et al., "Efficacy and satisfaction rate comparing endometrial ablation by rollerball electrocoagulation to uterine balloon thermal ablation in a randomised controlled trial" Eur J Obstet Cynecol Reprod Biol, May 10, 2004, pp. 97-103, vol. 114, No. 1. (Abstract).
Vargh Ese, T. et al., "Real-time calibration of temperature estimates during radio frequency ablation" Ultrason Imaging, Jul. 26, 2004, pp. 185-200. (Abstract).
Vilos, G.A., et al., "Characterization and mitigation of stray radio frequency currents during monopolar resectroscopic electrosurgery" J Minim Invasive Gynecol., Mar.-Apr. 2006, pp. 134-140, vol. 13, No. 2. (Abstract).
PCT International Preliminary Report on Patentability for International Application No. PCT/US2010/049186, mailed Apr. 19, 2012 (11 pages).

\* cited by examiner

METHOD AND APPARATUS FOR ENDOMETRIAL ABLATION IN COMBINATION WITH INTRAFALLOPIAN CONTRACEPTIVE DEVICES

FIELD

The invention relates generally to methods and apparatuses for endometrial ablation and intrafallopian tube contraceptive devices.

BACKGROUND

Menorrhagia is a condition in which a woman has extremely heavy menstrual periods or bleeding between periods. Also called dysfunctional uterine bleeding, menorrhagia is characterized by heavy and prolonged menstrual bleeding. Generally, bleeding is considered excessive when a woman soaks through enough sanitary products (sanitary napkins or tampons) to require changing every hour; while prolonged bleeding is when a woman experiences a menstrual period that lasts longer than seven days. In some cases, bleeding may be so severe and relentless that daily activities become interrupted and anemia develops.

Menorrhagia and abnormal uterine bleeding may be due to a hormone imbalance or disorder (particularly estrogen and progesterone), especially in women approaching menopause or after menopause. Other causes of abnormal bleeding include the presence of abnormal tissues such as fibroid tumors (benign tumors that develop in the uterus, also called myomas), polyps, or cancer of the endometrium or uterus. Two approaches to curing the symptoms of menorrhagia are hysterectomy, removal of the uterus, or, endometrial ablation.

Endometrial ablation is a procedure to permanently remove a thin tissue layer of the lining of the uterus to stop or reduce excessive or abnormal bleeding in women for whom childbearing is complete. Because the endometrial lining is destroyed, it can no longer function normally, and bleeding is stopped or controlled. In most cases, a woman cannot carry a fetus after endometrial ablation because the lining that nourishes a fetus has been removed. However, after ablation, a woman still has her reproductive organs and thus may still carry the risk of pregnancy because the sperm is still free to fertilize the eggs by traveling into the fallopian tubes.

Techniques used to perform endometrial ablation all involve the ultimate use of temperature to denature cell protein and thus destroy the endometrial tissue. These techniques generally include: hydrothermal (heated fluid pumped into the uterus), laser, balloon therapy (heating fluid in a balloon in contact with endometrial tissue), cryoablation (freezing), electrical or electrocautery, and radiofrequency or electrode (combination of vacuum and electrical current).

There are many options of permanent birth control available to women, including tubal ligation and vasectomy. However, the aforementioned procedures, though effective, are also invasive surgical procedures that require general anesthesia and surgical incision into the abdomen for laparoscopic access.

An alternate approach to permanent contraception is by placing a contraceptive device into the fallopian tubes. Placement of the intrafallopian contraceptive device does not require general anesthesia or surgical incision. Placement of the intrafallopian device is a less invasive procedure which carries a lower rate of risk or complication. This intrafallopian contraceptive device performs a contraception function by inducing tissue growth in the fallopian tubes thus blocking the spec leis from traveling into the fallopian tubes to fertilize the eggs.

The endometrial ablation procedure and the intrafallopian contraception procedure can be performed on the same woman. Women who elect to undergo a procedure for endometrial ablation generally seek sterilization because they do not want to risk the chance of pregnancy when the uterus cannot provide the fetus with sufficient nutrients. Similarly, although after receiving the intrafallopian contraceptive device a woman becomes sterile and cannot bear children, that does not preclude a woman from suffering from menorrhagia.

The available intrafallopian contraceptive devices are typically made of metal. That is, the intrafallopian contraceptive devices are made from conductive materials. In addition, when the intrafallopian contraceptive device is placed in the fallopian tube, at least a portion of the intrafallopian device may extend from the fallopian tube into the uterus (or substantially near the uterus).

As discussed above, a number of endometrial ablation devices require the use of electrical current and radiofrequency to generate heat to ablate the tissue. These ablation devices generally use an electrode or an antenna to conduct electricity or radiofrequency energy for ablation. Consequently, the placement of an electrode or an antenna in contact with endometrial tissue inside the uterus of a patient having an implanted intrafallopian contraceptive device runs the risk of short circuiting the electrode and/or heating other peripheral tissue if contact is made with the contraceptive device.

SUMMARY OF THE DESCRIPTION

Sterilization devices are described herein. In one embodiment, the sterilization device includes an implantable device having a proximal end and a distal end adapted to be positioned at least partially in a fallopian tube, wherein at least the proximal end of the implantable device is non-conductive.

In one embodiment, the sterilization device includes a resilient elongate body implantable into a fallopian tube having a proximal end and a distal end and defining an axis therebetween, wherein at least a portion of the body extendable from the fallopian tube into a uterus is non-conductive.

In one embodiment, the sterilization device includes an intraluminal body which is at least in part radially expandable about a longitudinal axis thereof within a lumen of a patient's reproductive system from a first transverse dimension to a second larger transverse dimension wherein at least a portion of the intraluminal body extendable from the lumen of the patient's reproductive system is non-conductive. In one implementation of an embodiment, the intraluminal body has a conductive portion at a proximal end and a non-conductive portion at only the distal end of the intraluminal body.

In one embodiment, the sterilization device includes an elongate body having a proximal end, a distal end, and a delivery lumen; a shaft slidably disposed within the delivery lumen of the elongate body; and an ablation element connected to the shaft to ablate uterine tissue, the ablation element comprising an insulator at portions of the ablation element that ablate tissue near the fallopian tubes.

In one embodiment, the sterilization device includes an elongate body having a proximal end, a distal end, and a delivery lumen; a shaft slidably disposed within the delivery lumen of the elongate body; and an ablation element connected to the shaft to ablate uterine tissue, a portion of the ablation element contactable with a contraceptive device implanted in a fallopian tube of a patient comprising an insulator.

A method of sterilizing reproductive tissue is also disclosed herein. In one embodiment, the method includes delivering an implantable device to a fallopian tube; inciting a tissue reaction of tubal tissues with an element (e.g., a tissue ingrowth reaction material) of the contraceptive device so as to affix the contraceptive device within the fallopian tube; delivering an ablation element to a uterus of a patient; and ablating at least a portion of the uterus, wherein at least a portion of the implantable device is non-conductive or a portion of the ablation element contactable with the implantable device includes an insulator.

The proximal end of the implantable device may be made from a non-conductive material, the proximal end of the sterilization device may include a non-conductive coating, and/or the sterilization device may be made from a non-conductive material. Both a portion of the implantable device may be non-conductive and a portion of the ablation element contactable with the implantable device may include an insulator.

BRIEF DESCRIPTION OF THE DRAWINGS

The invention is described by way of example with reference to the accompanying drawings, wherein.

DETAILED DESCRIPTION

Embodiments of the present invention relate to an intrafallopian contraceptive device which includes a non-conductive portion (e.g., only the proximal portion of the device) and/or includes a non-conductive coating (e.g., a non-conductive coating at only the proximal portion of the device). Embodiments of the present invention also relate to an ablation element for uterine ablation which includes non-conductive portions (e.g., non-conductive portions at only those portions which are adjacent to the fallopian tubes). Embodiments of the present invention also relates to systems and methods which may use the above-described intrafallopian device, ablation element and/or combinations thereof.

Figure 1:
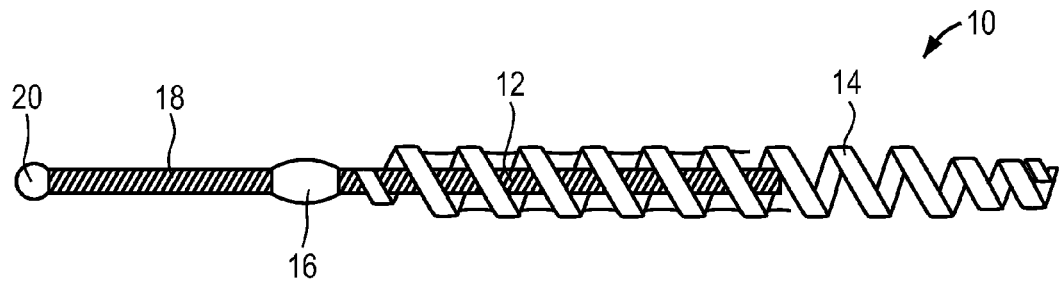
FIG. 1 is a side view of an implantable device in accordance with one embodiment of the invention.

FIG. 1 shows an intrafallopian contraceptive device 10 which can be used in accordance with one embodiment of the present invention. The intrafallopian device 10 includes a primary coil 12, a secondary coil 14 and a bond 16. The secondary coil 14 is disposed around the primary coil 12. The secondary coil 14 is affixed to the primary coil 12 at the bond 16. The primary coil 12 includes a distal portion 18 and a distal tip 20.

In one embodiment, the intrafallopian device 10 is completely or partially non-conductive. In particular, in one embodiment, each of the primary coil 12, secondary coil 14, bond 16, distal portion 18 and distal tip 20 are non-conductive. In one embodiment, the intrafallopian device 10 is made from a plastic material, such as, for example, a polymer, or other non-conductive materials, as known to those of skill in the art. In certain embodiments, the distal portion of the device 10 includes conductive materials while the proximal portions includes only non-conductive materials. For example, the secondary coil 14 may be formed from a non-conductive material while the remainder of the device includes at least one conductive material.

Figure 2:
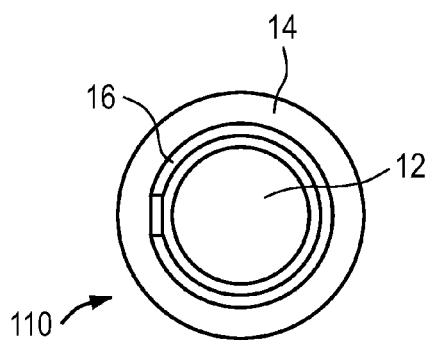
FIG. 2 is an end view of the implantable device of FIG. 1.

FIG. 2 shows the intrafallopian device 10 in a first configuration, in which the intrafallopian device 10 is delivered to the fallopian tube.

Figure 3:
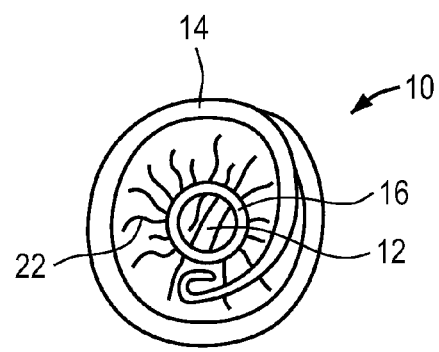
FIG. 3 is an end view of the implantable device of FIG. 1 after it has been deployed within a fallopian tube.

FIG. 3 shows the intrafallopian device 10 in a second configuration, in which the intrafallopian device 10 is deployed at the fallopian tube. Typically, when the intrafallopian device 10 is deployed at the fallopian tube, a tissue reaction of the tubal tissues of the fallopian tube is incited to affix the intrafallopian device 10 within the fallopian tube. The device 10 may include a material, such as polyethylene terephthalate (also known under the trade name DACRON®), which is designed to incite or promote tissue ingrowth into the device 10 and which will typically cause complete functional occlusion of the fallopian tube. In FIG. 3, fallopian tissue 22 is shown extending into the area of the device between the primary coil 12 and the secondary coil 14.

It will be appreciated that although the intrafallopian contraceptive device 10 disclosed has a configuration which includes a primary coil and a secondary coil affixed to the primary coil at a bond, the intrafallopian contraceptive device 10 may have other configurations, such as open walled stents, etc., as well as the configurations described in U.S. Patent Application Publication No. 2005/0274384, which is the published application of application Ser. No. 10/866,493, filed Jun. 10, 2004; this application is incorporated herein by reference.

Figure 4:
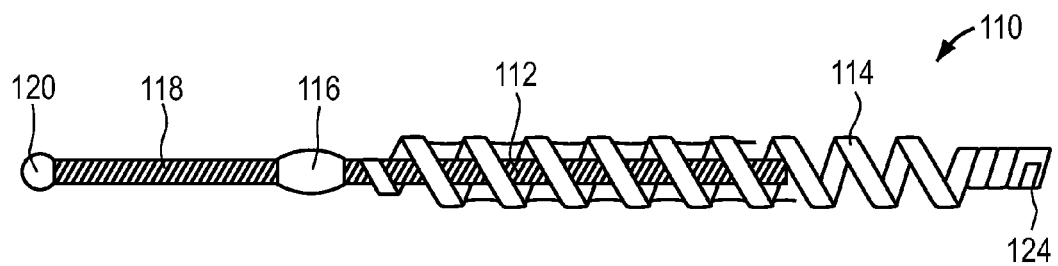
FIG. 4 is a side view of the implantable device in accordance with one embodiment of the invention.

FIG. 4 shows an alternative intrafallopian device 110 which can be used in accordance with one embodiment of the present invention. The intrafallopian device 110 includes a primary coil 112, a secondary coil 114 and a bond 116. The secondary coil 114 is disposed around the primary coil 112. The secondary coil 114 is affixed to the primary coil 112 at the bond 116. The primary coil 112 includes a distal portion 118 and a distal tip 120. In one embodiment, the secondary coil 114 includes a proximal tip 124, which may be non-conductive.

In one embodiment, a portion of the intrafallopian device 110 is non-conductive. In one embodiment, only the proximal end of the intrafallopian device 110 is non-conductive. In one embodiment, the coil 114 is non-conductive. In one embodiment, the distal portion 118 and distal tip 120 are conductive, while the coil 114 is non-conductive. In one embodiment, the distal tip 120 is non-conductive. In one embodiment, the non-conductive portion of the intrafallopian device 110 is made from a plastic material, such as, for example, a polymer, or other non-conductive materials, as known to those of skill in the art.

As described above with reference to intrafallopian device 10 and with reference, in particular, to FIGS. 2 and 3, the intrafallopian device 110 is also expandable from a first configuration in which the intrafallopian device 110 is delivered to the fallopian tube to a second configuration in which the intrafallopian device 110 is deployed at the fallopian tube.

It will be appreciated that although the intrafallopian contraceptive device 110 disclosed has a configuration which includes a primary coil and a secondary coil affixed to the primary coil at a bond, the intrafallopian contraceptive device 110 may have other configurations as described herein.

Figure 5:
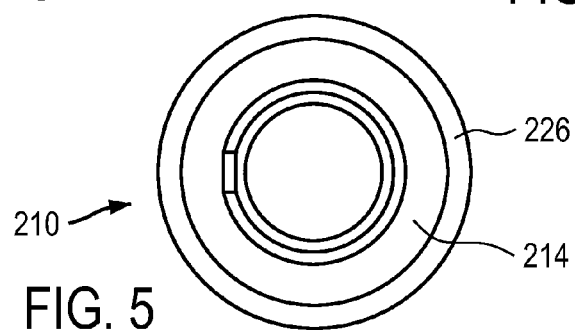
FIG. 5 is an end view of an implantable device in accordance with one embodiment of the invention.

FIG. 5 shows an alternative end view of an intrafallopian device 210. The intrafallopian device 210 includes a primary coil 212, a secondary coil 214 and a bond 216. The secondary coil 214 is disposed around the primary coil 212. The secondary coil 214 is affixed to the primary coil 212 at the bond 216. The intrafallopian device 210 also includes a non-conductive coating 226 on the primary coil 214.

In one embodiment, the non-conductive coating 226 is made from a plastic material, such as, for example, a polymer, or other non-conductive materials, as known to those of skill in the art.

As described above with reference to intrafallopian device 10 and with reference, in particular, to FIGS. 2 and 3, the intrafallopian device 210 is also expandable from a first configuration in which the intrafallopian device 210 is delivered to the fallopian tube to a second configuration in which the intrafallopian device 210 is deployed at the fallopian tube.

It will be appreciated that although the intrafallopian contraceptive device 210 disclosed has a configuration which includes a primary coil and a secondary coil affixed to the primary coil at a bond, the intrafallopian contraceptive device 210 may have other configurations as described herein.

Figure 6:
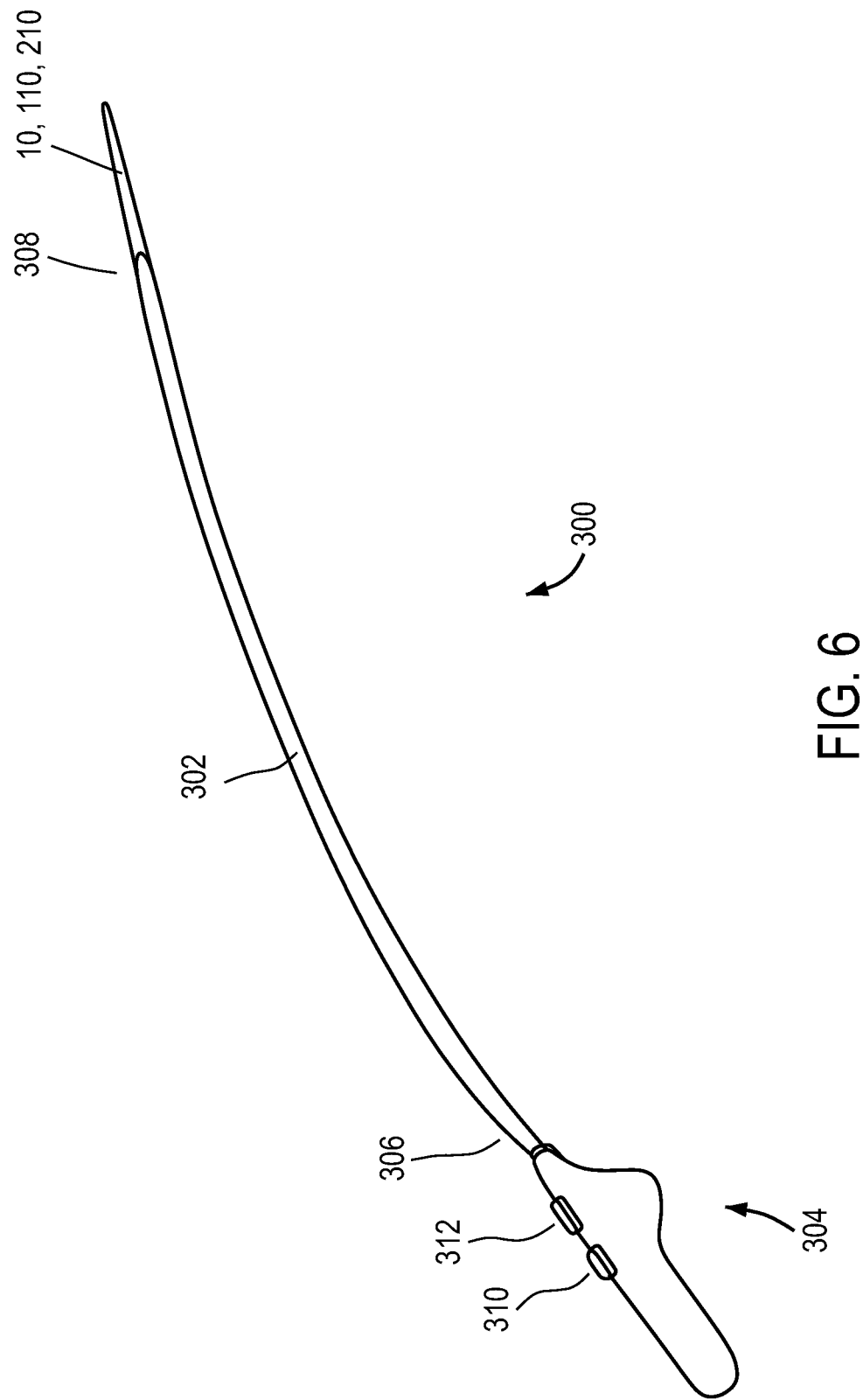
FIG. 6 is a side view of a delivery device for an implantable device in accordance with one embodiment of the invention.

FIG. 6 shows a delivery system 300, according to one embodiment, for delivering an intrafallopian device, such as, for example, intrafallopian devices 10, 110 and 210. The delivery system 300 includes a delivery catheter 302 and a delivery handle 304. The delivery catheter 302 includes a proximal end 306 and a distal end 308. An intrafallopian device, such as one of intrafallopian devices 10, 110, 210, is attached to the distal end of the delivery catheter 302. The delivery handle 304 is connected at the proximal end 306 of the delivery catheter 302. The delivery handle may include a release button 310 and a thumbwheel 312. The thumbwheel 312, in one embodiment, expands the intrafallopian device from a first, delivery configuration to a second, expanded configuration, when the intrafallopian device is positioned at the treatment site. The release button 310, in one embodiment, detaches the intrafallopian device from the distal end of the delivery catheter 302 when the intrafallopian device is positioned and expanded at the treatment site.

FIGS. 7A-7E show a method of implanting an intrafallopian device at a fallopian tube. In one embodiment, the intrafallopian device may be one of the intrafallopian devices 10, 110 or 210, described above with reference to FIGS. 1-5.

Figure 7A:
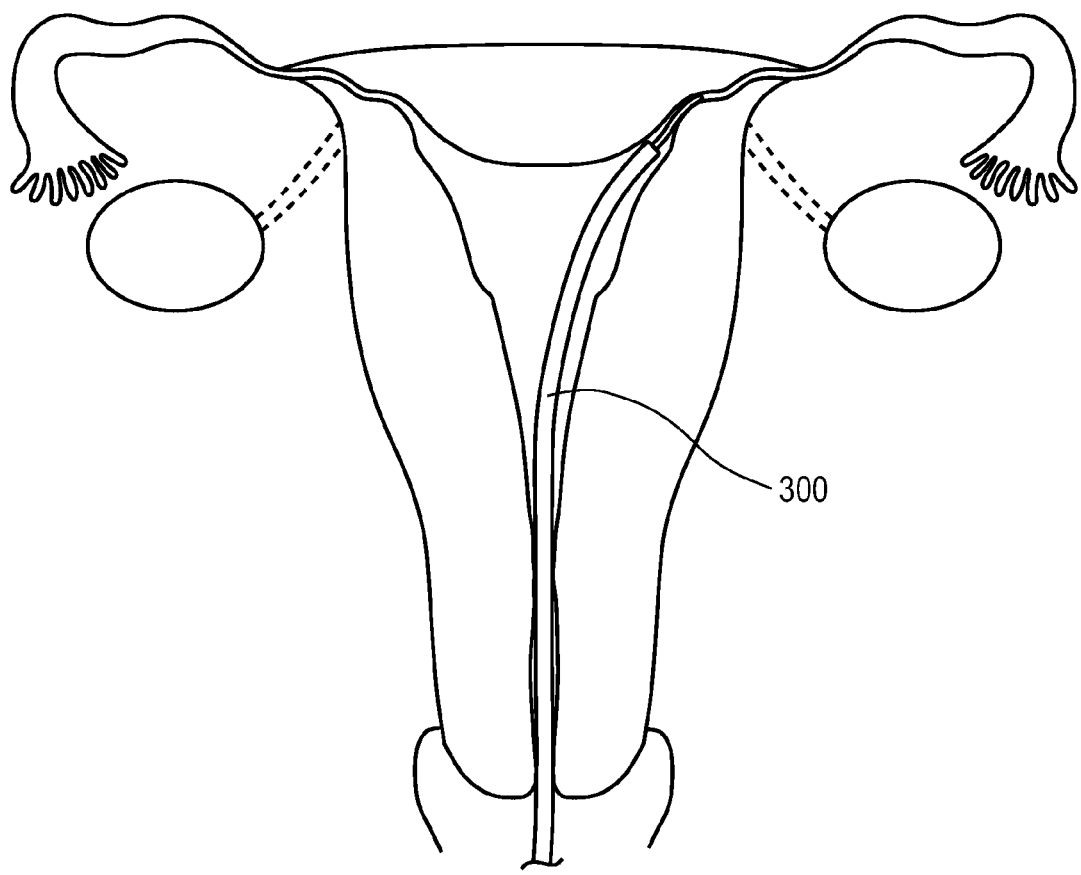
FIGS. 7A-7E are schematic views of delivery of an implantable device to a fallopian tube in accordance with one embodiment of the invention.
Figure 7B:
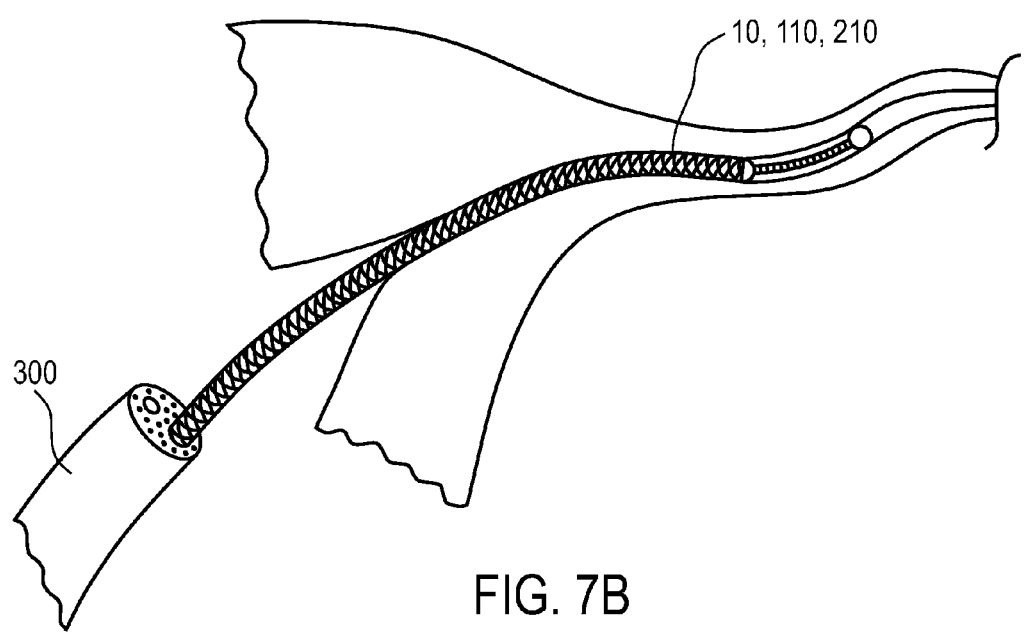
Figure 7C:
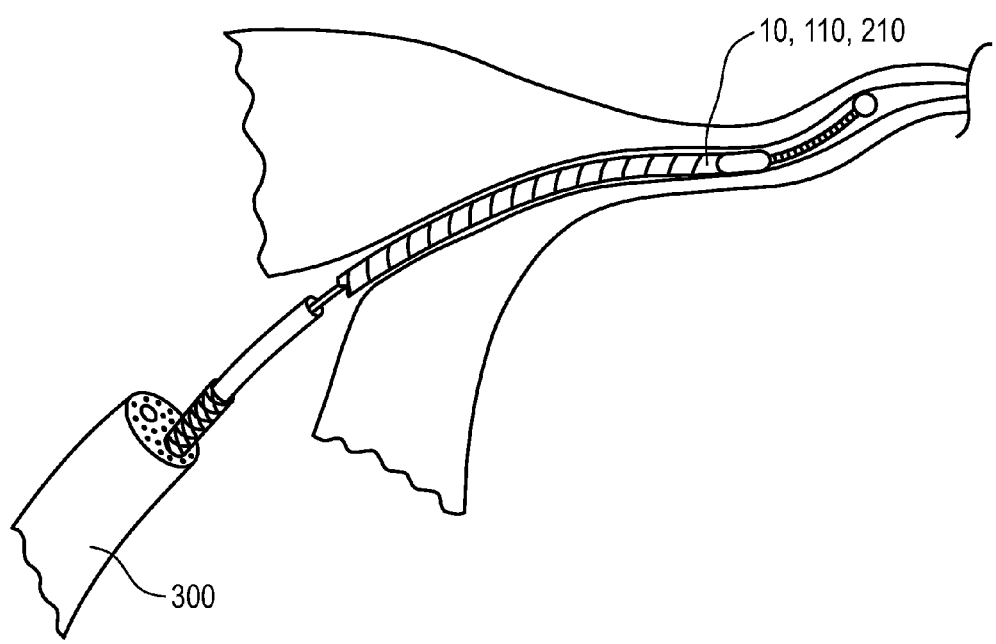

As shown in FIG. 7A, a delivery system, such as, for example, delivery system 300, is inserted into a female reproductive system to deliver an intrafallopian device to a fallopian tube through the patient's uterus. As shown in FIGS. 7B and 7C, the delivery system is used to advance the intrafallopian device into the fallopian tube in a first configuration.

Figure 7D:
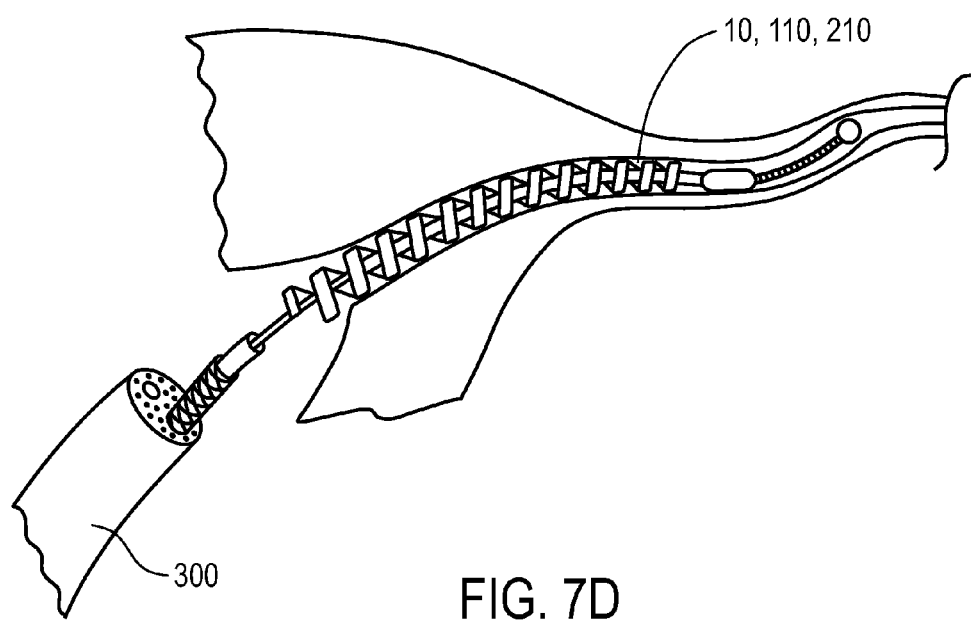

As shown in FIG. 7D, the intrafallopian device is expanded into a second configuration when the intrafallopian device is located at the appropriate location. It will appreciated that in some embodiments a portion of the intrafallopian device may extend into or be positioned substantially near the uterus of the patient.

Figure 7E:
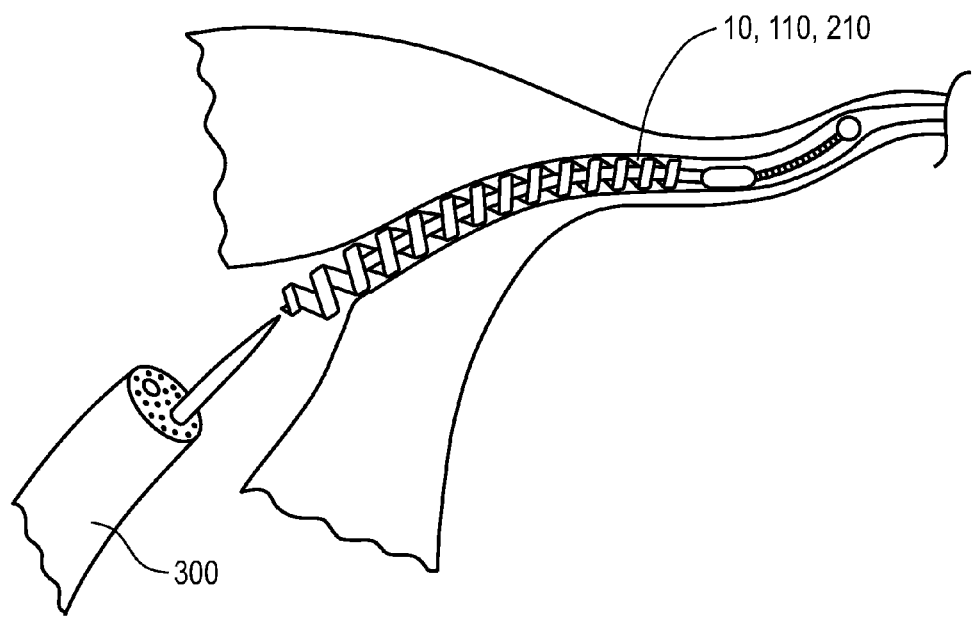

As shown in FIG. 7E, after the intrafallopian device is expanded, the intrafallopian device is detached or otherwise decoupled from the delivery system. As described above, it will appreciated that in some embodiments a portion, such as a proximal portion, of the intrafallopian device may extend into or be positioned substantially near the uterus of the patient. Typically, when the intrafallopian device is deployed in the fallopian tube, a tissue reaction of the tubal tissues of the fallopian tube is incited to affix the intrafallopian device within the fallopian tube.

Figure 8:
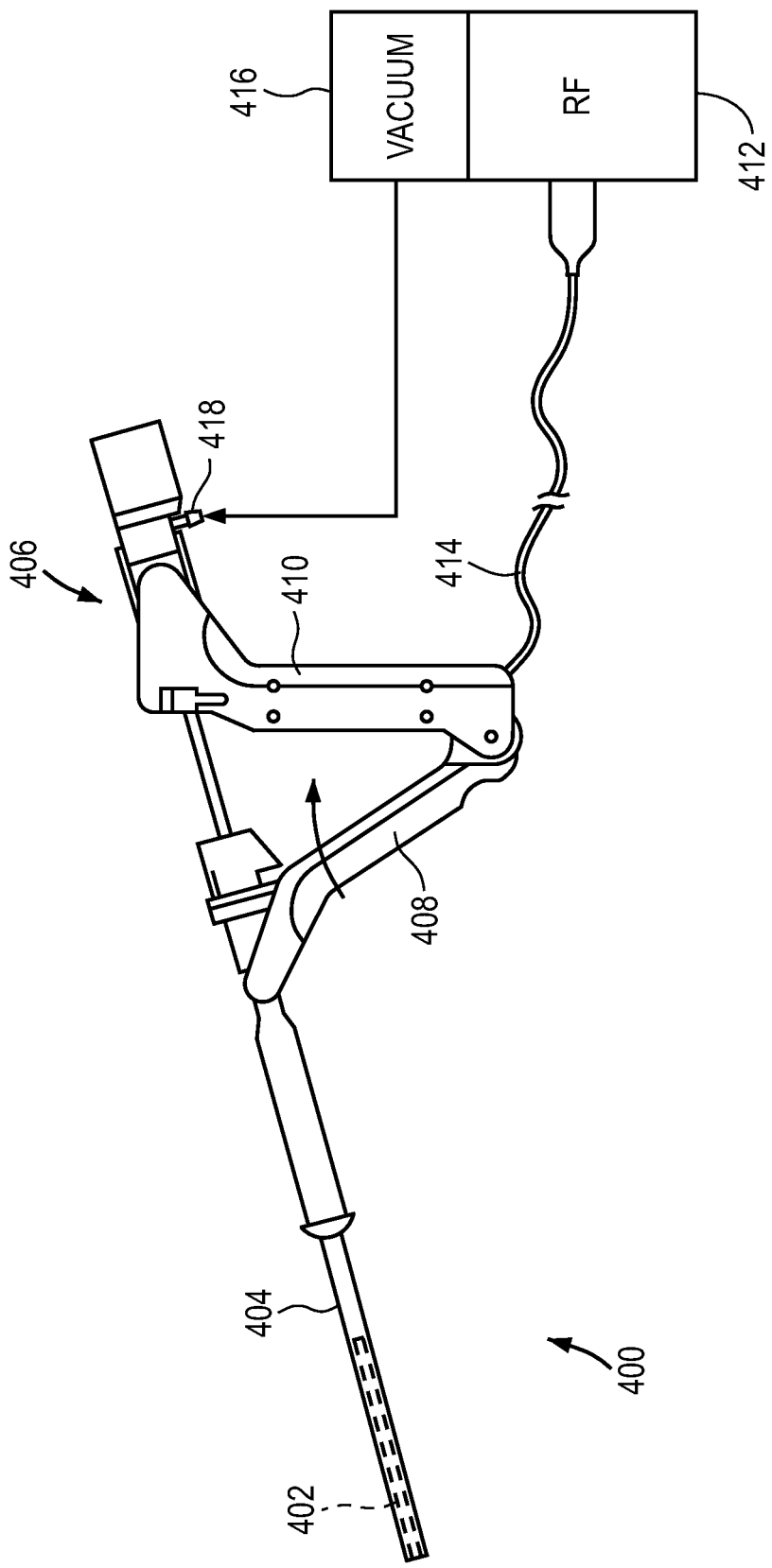
FIG. 8 is a side view of an ablation delivery system in accordance with one embodiment of the invention.

FIG. 8 shows an exemplary uterine ablation system 400 which can be used in accordance with one embodiment of the present invention. In one embodiment, the uterine ablation system 400 includes an ablation element 402, a sheath 404 and a handle 406. The handle 406 may include a first grip 408 and a second grip 410. The ablation system 400 may also include an RF (radio frequency) generator 412 connected to the handle via RF connector 414, and a vacuum source 416 connected to the handle 406 at vacuum port 418. The ablation element 402 is slidably disposed within the sheath 404 during insertion of the ablation system 400 into the uterine cavity, and the handle is subsequently manipulated to cause the ablation element 402 to extend from the distal end of the sheath 404.

Figure 9:
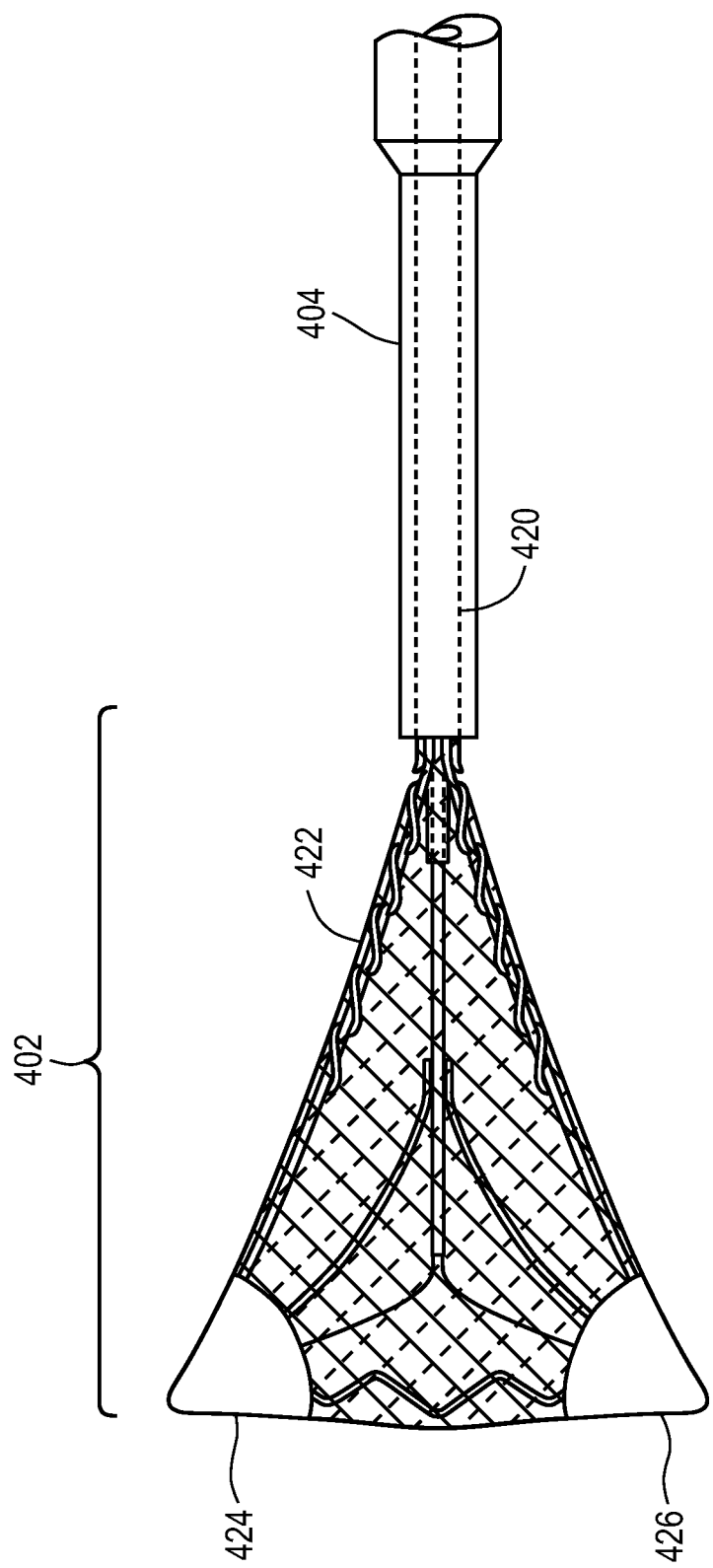
FIG. 9 is a detailed side view of the ablation delivery system of FIG. 7.

FIG. 9 shows the ablation element 402 of the uterine ablation system 400, in more detail, in an expanded configuration. The ablation element 402 includes a shaft 420 slideably disposed within the sheath 404. The ablation element 402 may also include an electrode array 422. In one embodiment, the electrode array 422 is formed from a stretchable metallized fabric mesh which may be knitted from a nylon and spandex knit plated with gold or other conductive material.

The ablation element 402 also includes non-conductive portions 424, 426 which are shown positioned generally at corners of the expanded ablation element 402, in the illustrated embodiment. In one embodiment, the non-conductive portions 424, 426 are positioned such that portions of the ablation element 402 that may come into contact with the fallopian tube are non-conductive. In one embodiment, the non-conductive portions 424, 426 are positioned such that portions of the ablation element 402 that could come into contact with an implantable device, such as, for example, a proximal portion of one of implantable devices 10, 110, 210, are non-conductive. In one embodiment, the non-conductive portions 424, 426 are formed by altering the ablation electrode 402, such as, for example, by using etching techniques to remove conductive metal from the mesh. In one embodiment, a non-conductive material may be secured to the ablation element 402. In one embodiment, the non-conductive portions 424, 426 are electrical insulators, which do not conduct electrical currents.

In one embodiment, the non-conductive material is a plastic material, such as, for example, a polymer, or another non-conductive material, as known to those of skill in the art.

In use, the ablation element 402 is delivered to a patient's reproductive system. The first grip 408 and second grip 410 are squeezed together to slide the ablation element 402 from the sheath 404. The RF generator 412 is then activated to deliver the ablation energy to the patient's uterus. The ablation element 402 can be configured into separate electrically conductive sections (e.g. two sections) which can receive power separately and independently in order to heat or ablate each corresponding section of the uterus separately and independently.

It will be appreciated that the ablation system may have a different configuration and/or employ an ablation technique other than the above-described ablation electrode.

Figure 10A:
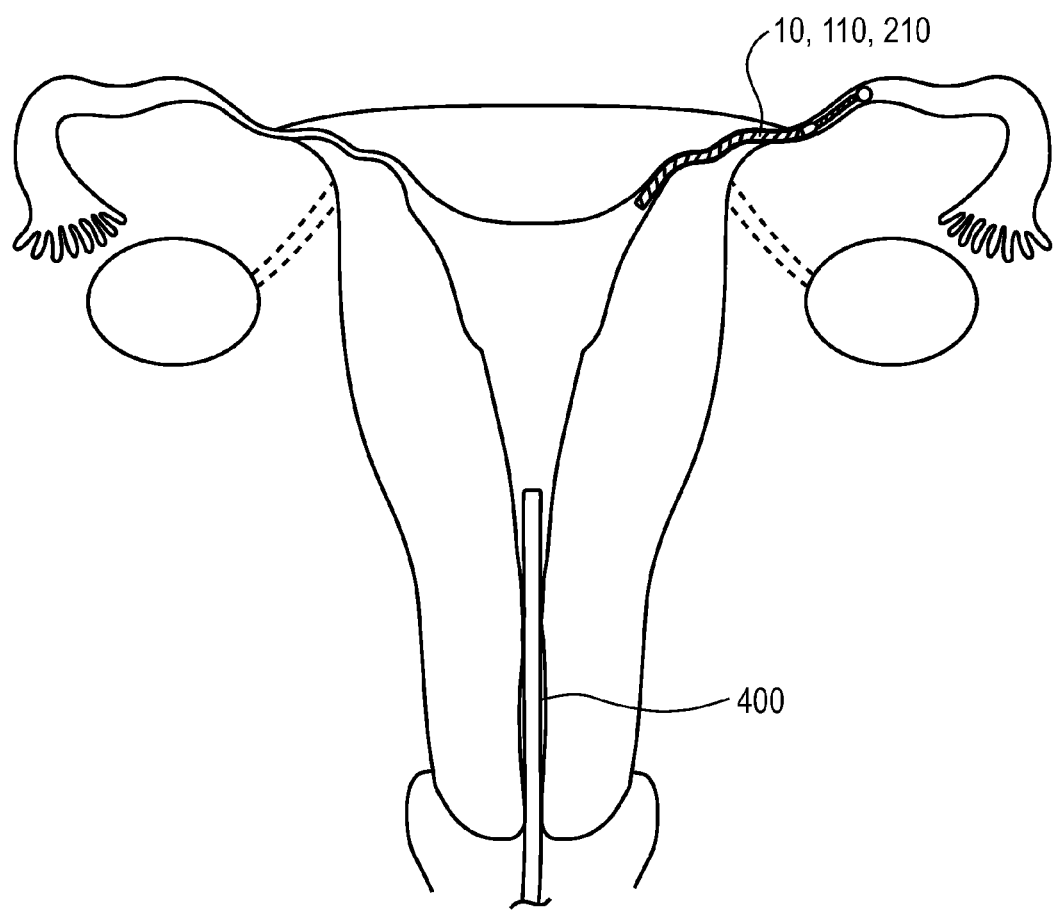
FIGS. 10A-10C are schematic views of delivery of the ablation system to a female reproductive system and ablation in accordance with one embodiment of the invention.
Figure 10B:
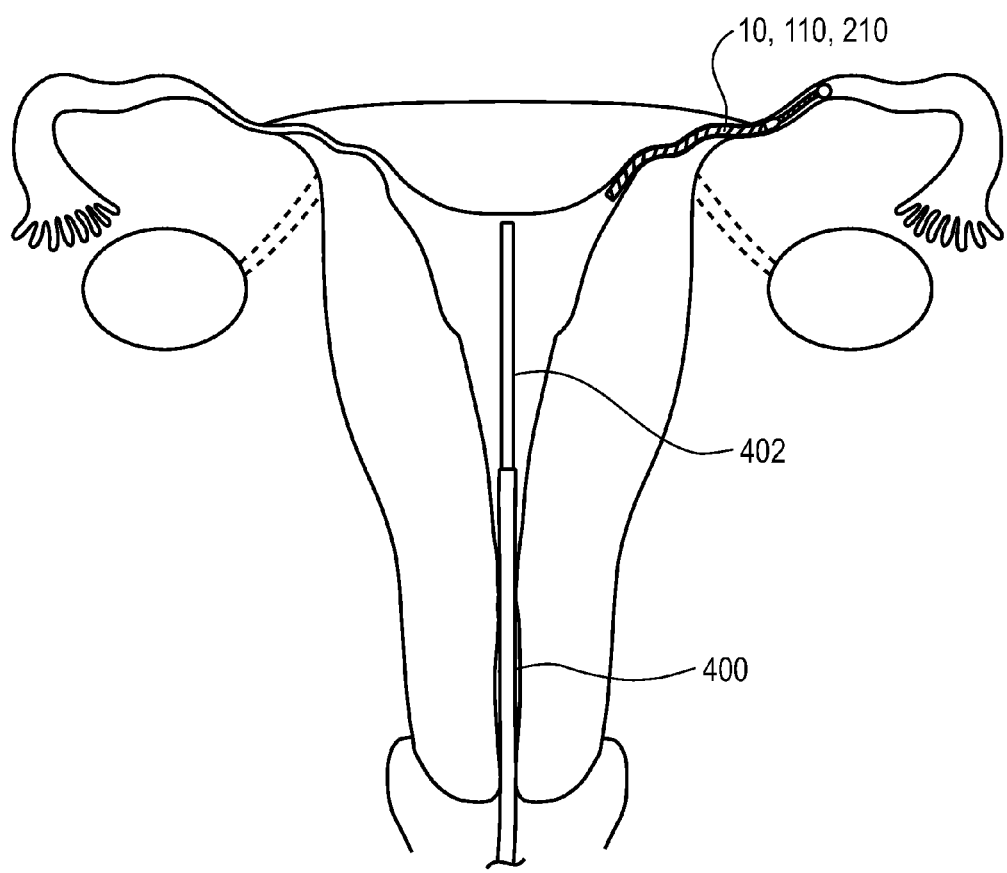
Figure 10C:
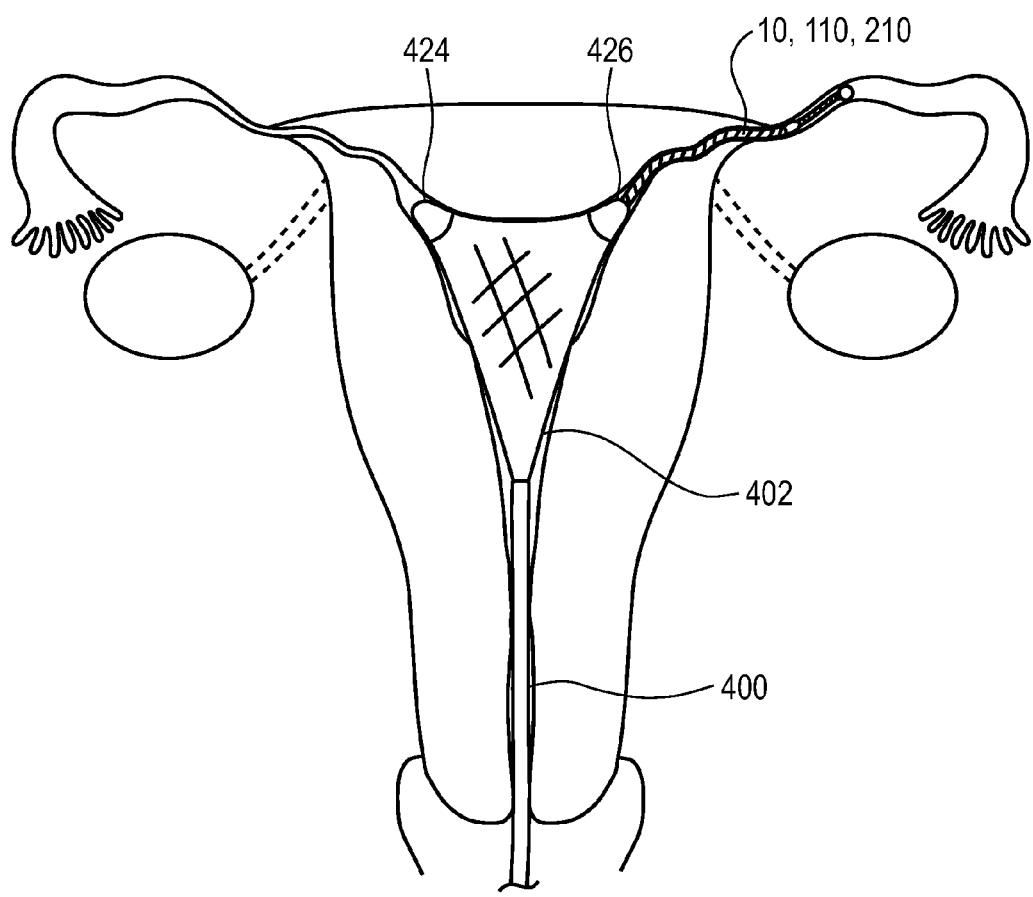

FIGS. 10A-10C show a method of ablating uterine tissue with an intrafallopian device, which is already deployed within a fallopian tube before the ablation procedure begins. As shown in FIG. 10A, an uterine ablation system, such as, for example, ablation system 400, is inserted into a female reproductive system. As shown in FIG. 10B, when the ablation system 400 is positioned, the ablation element 402 is extended to an ablation delivery position in the patient's uterus. As shown in FIG. 10C, the ablation element 402 is expanded to conform to the patient's uterus. In one embodiment, the portions of the ablation element 402 that include the non-conductive portions 424, 426 are the portions of the ablation element 402 that may come into contact with an implanted contraceptive device or are positioned near the fallopian tubes. As illustrated in FIG. 10C, the ablation element 402 is positioned in the uterus, the non-conductive portion 426 being positioned, generally, at or near the implantable device 10, 110, 210 or another implantable device. While FIGS. 10A-C show only an implanted contraceptive device in one fallopian tube, it will be understood that, in a typical procedure, there will be at least one implanted contraceptive device within each of the fallopian tubes before the ablation element is introduced into the uterus to perform the ablation.

Figure 11:
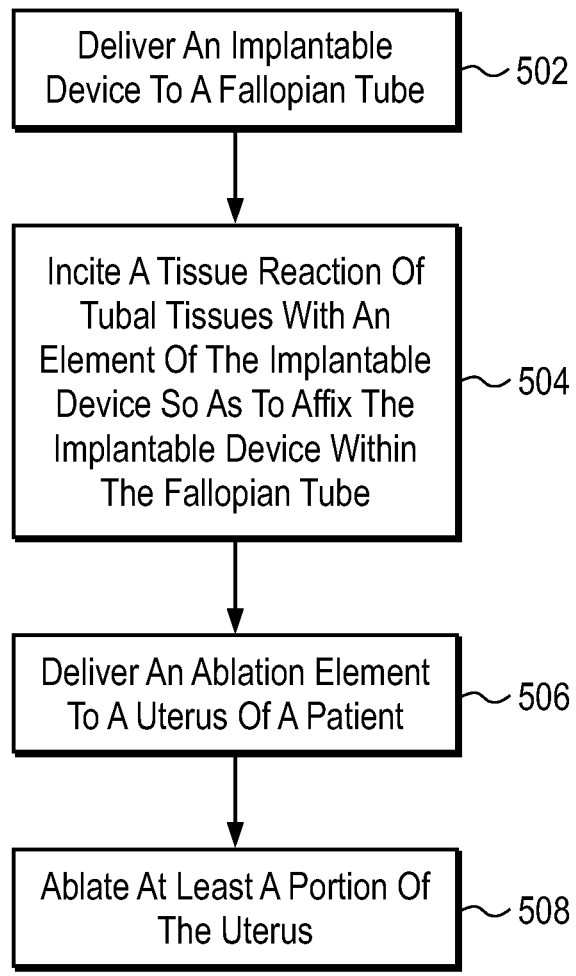
FIG. 11 is a flow chart of a sterilization method in accordance with one embodiment of the invention.

FIG. 11 shows a method for treating a female reproductive system in accordance with one embodiment of the present invention. The method begins at delivery operation 502, wherein an implantable device is delivered to a fallopian tube. A tissue reaction of tubal tissues may be incited with an element of the implantable device so as to affix the implantable device within the fallopian tube, at affixation operation 504. In one embodiment, the method continues at delivery operation 506, wherein an ablation element is delivered to a uterus of a patient after the implantable device has been deployed in the fallopian tube. The method continues at ablation operation 508 wherein at least a portion of the uterus is ablated. The implantable device may be non-conductive, include a non-conductive portion only at a proximal portion thereof and/or include a non-conductive coating only at a proximal portion thereof and/or the ablation element may include non-conductive portions. There are a variety of combinations which may be used in various methods of the invention. For example, in one case, the implantable device may have a conductive proximal portion while the ablation element has non-conductive portions which are deployed near the fallopian tubes and which are contactable with the implantable device. In another case, the implantable device may have a non-conductive proximal portion (e.g., a distal portion of the implantable device is conductive while a proximal portion, which may extend into the uterus, is non-conductive) and the ablation element includes conductive portions which are deployed near the fallopian tubes and which are contactable with the non-conductive proximal portion. In yet another case, the implantable device may have a non-conductive proximal portion and the ablation element has non-conductive portions which are deployed near the fallopian tubes and which are contactable with the implantable device.

The method shown in FIG. 11 assumes that the implantable device is first delivered to one or more fallopian tubes and is allowed to cause a tissue reaction (e.g. tissue ingrowth into the fallopian tube) before the ablation device is delivered to and used in the uterus. In an alternative embodiment, the ablation device can have two lumens or channels configured to receive one or more delivery catheters which deliver the implantable device, through the two lumens, to each fallopian tube. In this alternative embodiment, the ablation device can be deployed into the uterus before the implantable devices are implanted into their respective fallopian tubes; the lumens or channels are configured to guide the one or more delivery catheters through the cervix and the uterus, and a distal portion of each of the lumens or channels are open to direct the distal end of the delivery catheter into the ostium of a fallopian tube. Each distal portion of the lumen or channel can be located in one of the non-conductive portions 424 or 426 shown in FIG. 9 in order to have the opening of the distal portion directed at and facing the ostium. The ablation device (e.g. the device in FIG. 9 with lumens or channels for the one or more delivery catheters) can be deployed within a uterus and then the implantable devices can be deployed through the ablation device. The implantable device can be deployed into a fallopian tube before the ablation device is used to ablate the uterus or after the ablation device is used to ablate the uterus.

The foregoing description with attached drawings is only illustrative of possible embodiments of the described method and should only be construed as such. Other persons of ordinary skill in the art will realize that many other specific embodiments are possible that fall within the scope and spirit of the present idea. The scope of the invention is indicated by the following claims rather than by the foregoing description. Any and all modifications which come within the meaning and range of equivalency of the following claims are to be considered within their scope.

The invention claimed is:

1. A method of sterilizing reproductive tissue comprising:
   delivering an expandable ablation element to a uterus of a patient, the expandable ablation element comprising an electrode array portion, a pair of non-conductive portions, and a pair of delivery lumens in the pair of non-conductive portions;
   expanding the ablation element to conform to the uterus with the pair of non-conductive portions occupying a pair of corner regions of the expanded ablation element adjacent a pair of ostia of a pair of fallopian tubes such that the electrode array does not contact the ostia;
   delivering an implantable device to one of the fallopian tubes through one of the delivery lumens in one of the non-conductive portions of the expanded ablation element;
   inciting a tissue reaction of the fallopian tube with an element of the implantable device so as to affix the implantable device within the fallopian tube; and
   ablating the uterus using the electrode array portion.

2. The method of claim 1, wherein a portion of the implantable device is non-conductive, and wherein a portion of the one of the pair of non-conductive portions contacts the implantable device.

3. The method of claim 1, wherein the implantable device comprises a distal end and a proximal end, and wherein the proximal end of the implantable device is non-conductive.

4. The method of claim 1, wherein a portion of the implantable device is non-conductive and extends into the uterus.

5. The method of claim 1, wherein the implantable device is non-conductive.

6. A sterilization device comprising:

a sheath having a proximal end and a distal end;

a shaft slidably disposable within the sheath; and an ablation element connected to the shaft to ablate uterine tissue, the ablation element comprising an electrode array portion and a pair of non-conductive portions, the ablation element being expandable to conform to a uterus such that each non-conductive portion occupies a different corner region of the expanded ablation element in contact with a different ostium of a pair of fallopian tubes such that the electrode array portion does not come into contact with the ostia.

7. The sterilization device of claim 6, wherein each of the pair of non-conductive portions comprises a delivery lumen such that a pair of openings in the pair of non-conductive portions face the pair of ostia when expanded to conform to the uterus.

8. The sterilization device of claim 7, further comprising:

a delivery catheter slidably disposable within one of the delivery lumens of the pair of non-conductive portions; and an implantable device connected to the delivery catheter to be positioned in one of the fallopian tubes.

9. The sterilization device of claim 8, further comprising:

a second delivery catheter slidably disposable within one of the delivery lumens of the pair of non-conductive portions; and a second implantable device connected to the second delivery catheter to be positioned in one of the fallopian tubes.

10. The sterilization device of claim 8, wherein the implantable device comprises a proximal device end and a distal device end adapted to be positioned in one of the fallopian tubes.

11. The sterilization device of claim 10, wherein at least the proximal device end is non-conductive.

12. The sterilization device of claim 11, wherein the proximal device end is made from a non-conductive material.

13. The sterilization device of claim 11, wherein the proximal device end comprises a non-conductive coating.

* * * * *